US009638682B2

(12) United States Patent
Hoff et al.

(10) Patent No.: US 9,638,682 B2
(45) Date of Patent: May 2, 2017

(54) METHOD FOR FAST ESTIMATION OF DISTILLATION RESIDUES AND COKE CHARACTERISTICS

(71) Applicant: IFP Energies nouvelles, Rueil-Malmaison (FR)

(72) Inventors: Anne Hoff, Trondheim (NO); Violaine Lamoureux-Var, Chatou (FR); Trygve Meyer, Stavanger (NO); Daniel Pillot, St Germain en Laye (FR)

(73) Assignee: IFP ENERGIES NOUVELLES, Rueil-Malmaison (FR)

( * ) Notice: Subject to any disclaimer, the term of this patent is extended or adjusted under 35 U.S.C. 154(b) by 79 days.

(21) Appl. No.: 14/548,491

(22) Filed: Nov. 20, 2014

(65) Prior Publication Data

US 2015/0135806 A1    May 21, 2015

(30) Foreign Application Priority Data

Nov. 20, 2013   (FR) ...................................... 13 61389

(51) Int. Cl.
    *G01N 33/28*      (2006.01)
(52) U.S. Cl.
    CPC ....... *G01N 33/287* (2013.01); *G01N 33/2823* (2013.01)
(58) Field of Classification Search
    CPC .......................... G01N 33/287; G01N 33/2823
    USPC ...................................................... 73/53.05
    See application file for complete search history.

(56) References Cited

U.S. PATENT DOCUMENTS

| 5,843,787 A * | 12/1998 | Trabelsi ............... G01N 33/241 436/139 |
| 2011/0263034 A1* | 10/2011 | Espitalie ................ G01N 33/24 436/122 |

FOREIGN PATENT DOCUMENTS

| FR | 2722296 A1 | 1/1996 |
| WO | 2010/049609 A1 | 5/2010 |

OTHER PUBLICATIONS

F. Behar et al. Rock-Eval 6 Technology: Performances and Developments, Oil & Gas Science and Technology-Rev. IFP, 2001, pp. 111-134, vol. 56, No. 2.

* cited by examiner

*Primary Examiner* — Daniel S Larkin
(74) *Attorney, Agent, or Firm* — Fitch, Even, Tabin & Flannery, LLP

(57) ABSTRACT

The present invention relates to a method of estimating, for a petroleum feedstock, values representative of the sulfur and carbon distributions in atmospheric and vacuum distillation residues, and a value representative of the sulfur content in coke. According to the method, the following stages are carried out:
  from a feedstock sample, measuring at least the Rock-Eval parameters S2b, $\text{Sulf}_{S2b}$, RC, $\text{Sulf}_{oxy}$ using a Rock-Eval device comprising a sulfur measurement module,
  deducing from the measurements of these Rock-Eval parameters the values of the sulfur and carbon distributions ($S^{PHF}$, $S^{COKE}$, $C^{PHF}$, $C^{COKE}$) in the distillation residues, and a sulfur content in relation to the carbon content in the coke.

4 Claims, 4 Drawing Sheets

METHOD FOR FAST ESTIMATION OF DISTILLATION RESIDUES AND COKE CHARACTERISTICS

FIELD OF THE INVENTION

The field of the invention relates to a method using a Rock-Eval™ apparatus (IFPEN) comprising a device for quantitative sulfur characterization (Rock-Eval Sulfur). From the analysis of a sample of some milligrams of raw sulfur-containing petroleum products, this method allows to estimate the values of: —the sulfur and carbon distribution in the atmospheric residue and the vacuum residue, and —the richness in sulfur of the coke in relation to the carbon content in coke, after distillation of this raw petroleum product.

This method is particularly intended for the sphere of petroleum product refining, but it can also apply to any technical field where the quantification of sulfur and/or of carbon and of their thermal reactivity in a solid or liquid product is required.

BACKGROUND OF THE INVENTION

Document WO-2010/049,609 notably describes the Rock-Eval method and process for sulfur analysis. The Rock-Eval is a device comprising at least one oven for pyrolysis in an inert atmosphere and at least one oxidation oven. A sulfur measurement module is in particular added to this device for sulfur analysis.

The prior art relative to refining for estimating the sulfur and carbon content of distillation residues can notably be:
 a. The total sulfur in crude oils and in crude oil distillation fractions is conventionally measured using the ASTM D4294 (XR Fluorescence) and ASTM D5453 (UV Fluorescence) methods.
 b. The carbon in crude oils and in crude oil distillation fractions is measured using the ASTM D5291 method.
 c. The coke potential of the residues is measured using the ASTM D189 (Conradson Carbon Residue CCR) and ASTM D4530 (Micro Carbon Residue MCR) methods.

Coke as such is not present in crude oil before it is processed by thermal cracking and it is therefore not measured in the crude. However, the potential coke to be generated varies from one crude to the next and it can be measured according to conventional methods that are relatively long and complex. The present invention allows these drawbacks to be overcome.

SUMMARY OF THE INVENTION

The invention relates to a method of estimating, for a petroleum feedstock, values representative of the sulfur and carbon distributions in atmospheric and vacuum distillation residues, and a value representative of the sulfur content in coke, wherein the following stages are carried out:
 from a feedstock sample, measuring at least parameters S2b, $Sulf_{S2b}$, RC, $Sulf_{oxy}$ using a device comprising at least one oven for pyrolysis in an inert atmosphere and at least one oxidation oven, said device comprising a sulfur measurement module, S2b being the mass proportion of heavy pyrolyzable compounds contained in said sample, $Sulf_{S2b}$ being the mass proportion of sulfur in the heavy pyrolyzable compounds contained in said sample, RC being the mass proportion of carbon of the pyrolysis residue of said sample, and $Sulf_{oxy}$ being the mass proportion of sulfur in the pyrolysis residue of said sample, deducing from said measurements of said parameters said values of the sulfur and carbon distributions in the distillation residues, and a sulfur content in relation to the carbon content in the coke.

According to the method, said representative values can be determined as follows (in g/g):
 $S^{PHF} = Sulf_{S2b}/[Sulf_{S2b}+Sulf_{oxy}]$, where $S^{PHF}$ corresponds to the proportion of sulfur in the pyrolyzable heavy fraction, with said parameters $Sulf_{S2b}$, $Sulf_{S2b}$ and $Sulf_{oxy}$ expressed in gram per gram of said sample,
 $S^{COKE} = Sulf_{oxy}/[Sulf_{S2b}+Sulf_{oxy}]$, where $S^{COKE}$ corresponds to the proportion of sulfur in the coke, with said parameters $Sulf_{S2b}$, $Sulf_{S2b}$ and $Sulf_{oxy}$ expressed in gram per gram of said sample,
 with $S^{PHF}+S^{COKE}=1$
 $C^{PHF} = S2b*0.083/[S2b*0.083+RC]$, where $C^{PHF}$ corresponds to the proportion of carbon in the pyrolyzable heavy fraction, with said parameters S2b and RC expressed in gram per gram of said sample,
 $C^{COKE} = RC/[S2b*0.083+RC]$, where $C^{COKE}$ corresponds to the proportion of carbon in the coke, with said parameters S2b and RC expressed in gram per gram of said sample,
 with $C^{PHF}+C^{COKE}=1$.

The value representative of the richness in sulfur in relation to the carbon content in the coke can be determined with:
 $Sulf_{oxy}/RC$, with said parameters $Sulf_{oxy}$ and RC expressed in gram per 100 grams of said sample.

Thus, by means of simple Rock-Eval type measurements, refiners can rapidly obtain useful information on the distribution of the sulfur among the pyrolyzable products and the coke from different types of petroleum products.

BRIEF DESCRIPTION OF THE FIGURES

Other features and advantages of the invention will be clear from reading the description hereafter, given by way of non limitative example, with reference to the accompanying figures wherein:

FIG. 1a: relates to the organic products measured by a flame ionization detector (FID),
FIG. 1b: relates to the $SO_2$ measured by a UV detector after oxidation of the pyrolysis effluents, FIGS. 2a, 2b, 2c give the measurements of the compounds released during the oxidation of the pyrolysis residue of a sulfur-containing petroleum product, with the Rock-Eval Sulfur device (as described in document WO-2010/049, 609), as a function of the temperature of the sample (vertical axis to the right) and of the heating time (horizontal axis)

DETAILED DESCRIPTION

In this method, a petroleum product sample is analyzed using the Rock-Eval apparatus provided with a device for measuring sulfur. The whole device is described in detail in patent WO-2010/049,609.

Figure 1A:
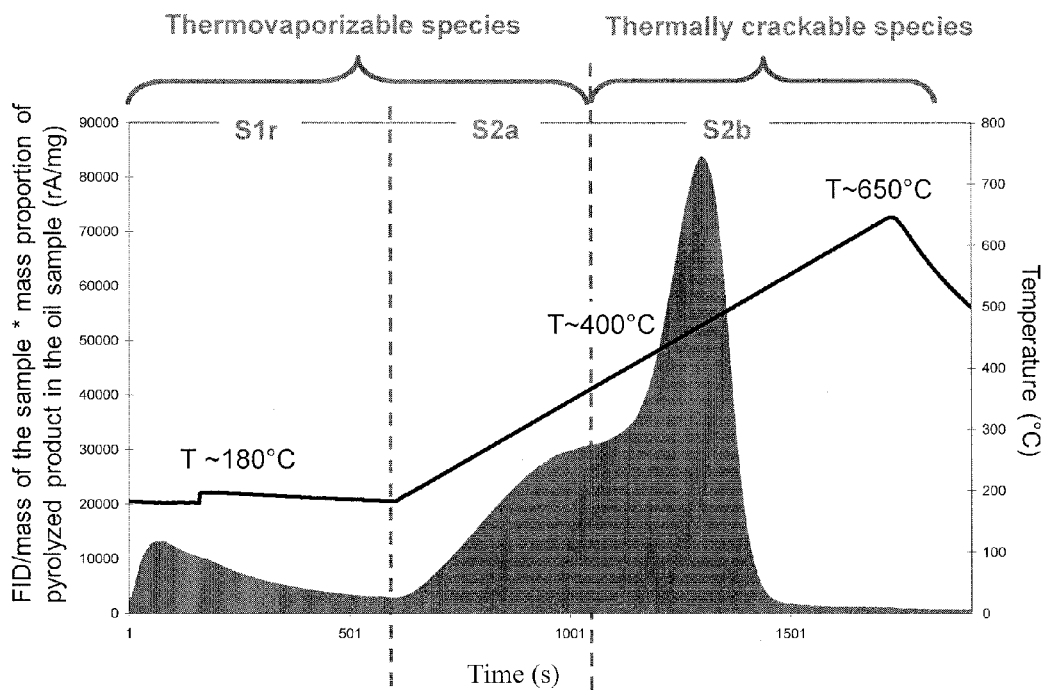
FIGS. 1a and 1b give the measurements of the compounds released during the pyrolysis of a sulfur-containing petroleum product, with the Rock-Eval provided with a device for analyzing sulfur (as described in document WO-2010/049, 609), as a function of the temperature of the sample (vertical axis to the right) and of the heating time (horizontal axis)

In this method, depending on the type of product analyzed, between 3 mg and 15 mg of feedstock are required per analysis. The sample is placed in a boat of the Rock-Eval apparatus between two finely crushed silica layers. The analysis is carried out in two automated stages. The first stage, referred to as pyrolysis, consists in heating the petroleum product sample in a continuous inert gas stream, which can be nitrogen. The temperature of the sample rises from an initial temperature ranging between 100° C. and 180° C. to a final temperature ranging between 650° C. and 800° C., while following a predetermined temperature program. During this first stage, the petroleum product sample releases carbon-containing and sulfur-containing effluents that are carried along by the inert gas stream towards specific analyzers where they are subjected to continuous measurement. FIG. 1a shows the peaks measured in a well-known manner, S1r, S2a, S2b that characterize the hydrocarbon-containing compounds. Peaks S1r and S2a result from the thermovaporization of the petroleum product, and peak S2b results from the thermal cracking of the petroleum product.

Figure 1B:
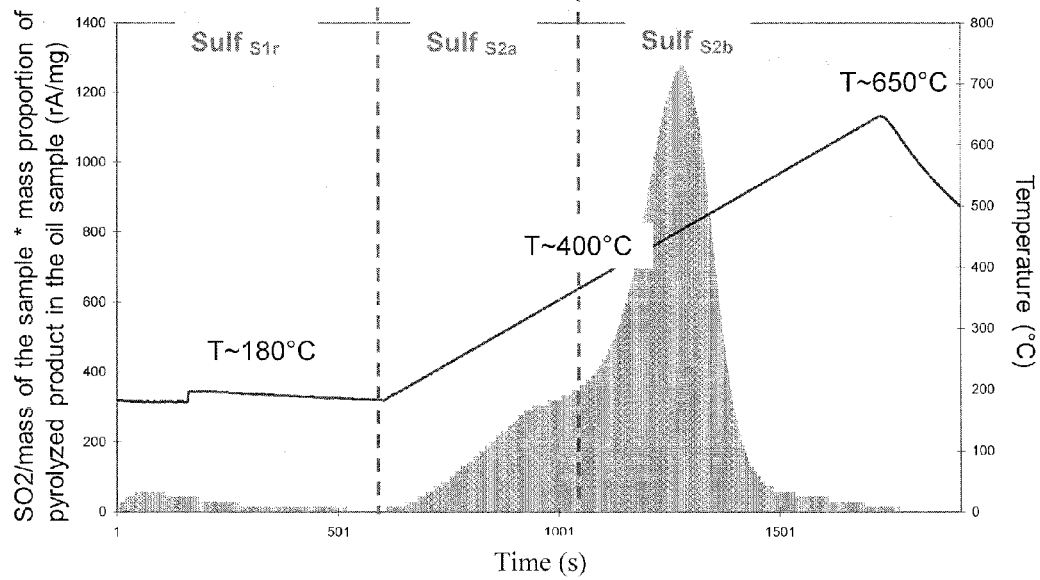

At the same time, a fraction of the pyrolysis effluents enters an oxidation oven. The sulfur contained in these effluents is then oxidized to $SO_2$ and it is sent to the specific analyzer to be subjected to continuous measurement. An example of the result of this measurement is shown in FIG. 1b.

At the end of the pyrolysis process, a petroleum product residue referred to as pyrolysis residue remains in the bottom of the boat. This residue is transferred in its boat to an oxidation oven. The second stage of the analysis is referred to as oxidation and it consists in heating the pyrolysis residue in a continuous air stream according to a predetermined temperature program. The initial temperature ranges between 300° C. and 400° C., and the final temperature ranges between 700° C. and 1200° C. depending on the type of product analyzed.

Figure 2A:
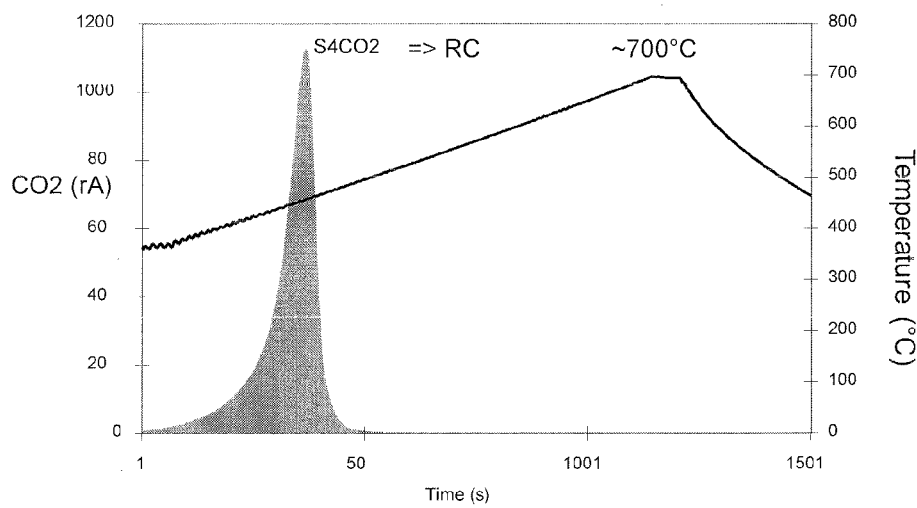
FIG. 2a: $CO_2$ measured by a UV detector.

During this second stage, the pyrolysis residue of the sample is oxidized and it releases carbon-containing and sulfur-containing gases that are carried along by the air stream towards the specific analyzers where they are subjected to continuous measurement. An example of the result of these measurements is shown in FIGS. 2a, b and c: (a) $CO_2$ measurement, (b) CO measurement, and (c) $SO_2$ measurement. Various base parameters characterizing the sulfur and the carbon of the petroleum product, in particular $Sulf_{oxy}$ and RC, are deduced from this analysis. In this method, the Rock-Eval calibration is performed beforehand by means of standard gases containing CO, $CO_2$ and $SO_2$, and reference petroleum products whose carbon and sulfur elements content is known.

Among the base parameters provided by the Rock-Eval Sulfur device, four parameters are used in this method:

S2b defines the mass proportion of heavy pyrolyzable compounds in the petroleum product sample.

It is the mass of organic compounds released by the sample through thermal cracking during the pyrolysis stage between approximately 400° C. and the final pyrolysis temperature (FIG. 1a) in relation to the initial mass of the petroleum product sample. These organic compounds are the heaviest compounds of the pyrolyzable oil fraction. From this parameter, it is possible to estimate the mass proportion of carbon in the heavy pyrolyzable compounds, assuming that the carbon mass content of these compounds is 83%.

S2b is generally given in the following unit: g (organic compounds)/1000 g (sample).

$Sulf_{S2b}$ defines the mass proportion of sulfur in the heavy pyrolyzable compounds of the petroleum product sample.

It is the mass of sulfur released by the sample during thermal cracking in the pyrolysis stage that is conducted between approximately 400° C. and the final pyrolysis temperature (FIG. 1b), simultaneously with the release of the organic products of peak S2b, in relation to the initial mass of the petroleum product sample.

$Sulf_{S2b}$ is generally given in the following unit: g (Sulfur)/100 g (sample).

RC (residual carbon) defines the mass proportion of carbon of the pyrolysis residue in the petroleum product sample.

Figure 2B:
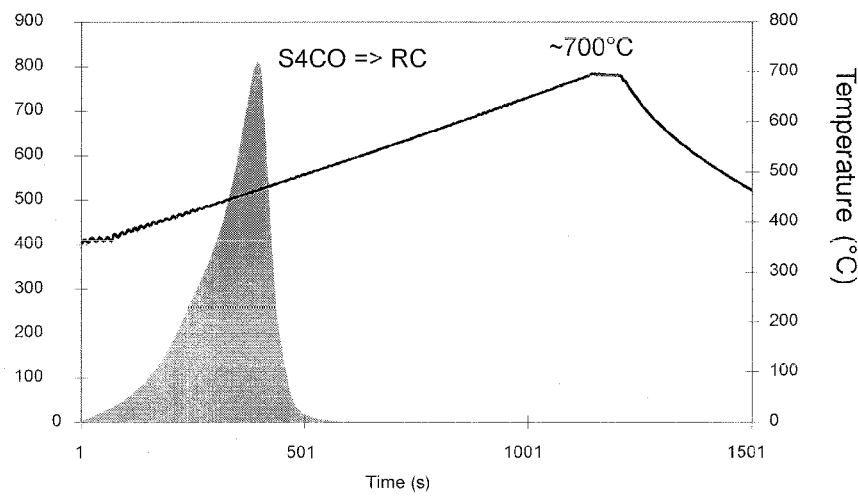
FIG. 2b: CO measured by a UV detector.

It is the mass of carbon in the residual sample after pyrolysis, in relation to the initial mass of the petroleum product sample; this carbon is released during the stage of oxidation of the pyrolysis residue, between 350° C. and the maximum oxidation temperature that can range between 700° C. and 1200° C. depending on the temperature program selected (FIGS. 2a and 2b). RC is calculated from the measurements of S4$CO_2$ and S4CO with the following formula for example:

$$RC = S4CO_2 \times 12/440 + S4CO \times 12/280, \text{ where:}$$

S4$CO_2$ is the $CO_2$ peak measured during the oxidation stage, in mg ($CO_2$)/g (sample), S4CO is the CO peak measured during the oxidation stage, in mg (CO)/g (sample).

RC is generally given in the following unit: g (C)/100 g (sample).

$Sulf_{oxy}$ defines the mass proportion of sulfur in the pyrolysis residue of the petroleum product sample.

Figure 2C:
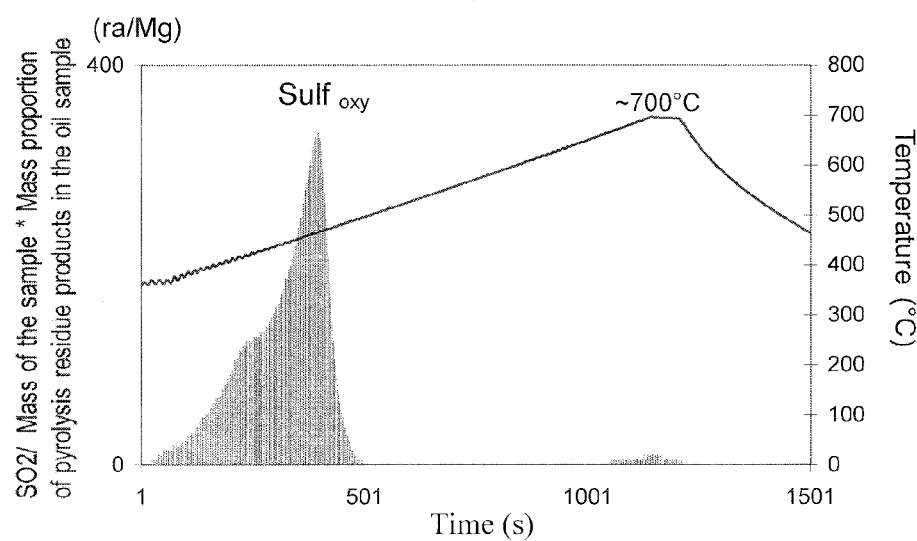
FIG. 2c: $SO_2$ measured by a UV detector, FIG. 3 gives the carbon level measured with Rock-Eval on a pyrolysis residue (vertical axis) as a function of the carbon level measured with the conventional Micro Carbon Residue measurement method—MCR, ASTM D4530 (horizontal axis), FIG. 4 gives the $SO_2$ signal during the pyrolysis of heavy oil A, of its atmospheric residue, of its vacuum residue and of its asphaltenes, FIG. 5 gives the $SO_2$ signal during the oxidation of heavy oil A, of its atmospheric residue, of its vacuum residue and of its asphaltenes.

It is the mass of residual sulfur after pyrolysis in relation to the initial sample mass; this sulfur is released during the oxidation of the pyrolysis residue, between 350° C. and the maximum oxidation temperature (FIG. 2c), simultaneously with the release of the residual carbon RC.

$Sulf_{oxy}$ is generally given in the following unit: g (Sulfur)/100 g (sample).

The organic compounds that are released during the pyrolysis between approximately 400° C. and the final pyrolysis temperature, which are characterized by parameters S2b (for carbon) and $Sulf_{S2b}$ (for sulfur), come from the pyrolyzable heavy fraction of the petroleum product analyzed that is thermally crackable.

The organic compounds that are released during the oxidation of the pyrolysis residue, which are characterized by parameters RC (for carbon) and $Sulf_{oxy}$ (for sulfur), come from the non-pyrolyzable heavy fraction of the petroleum product analyzed.

Figure 3:
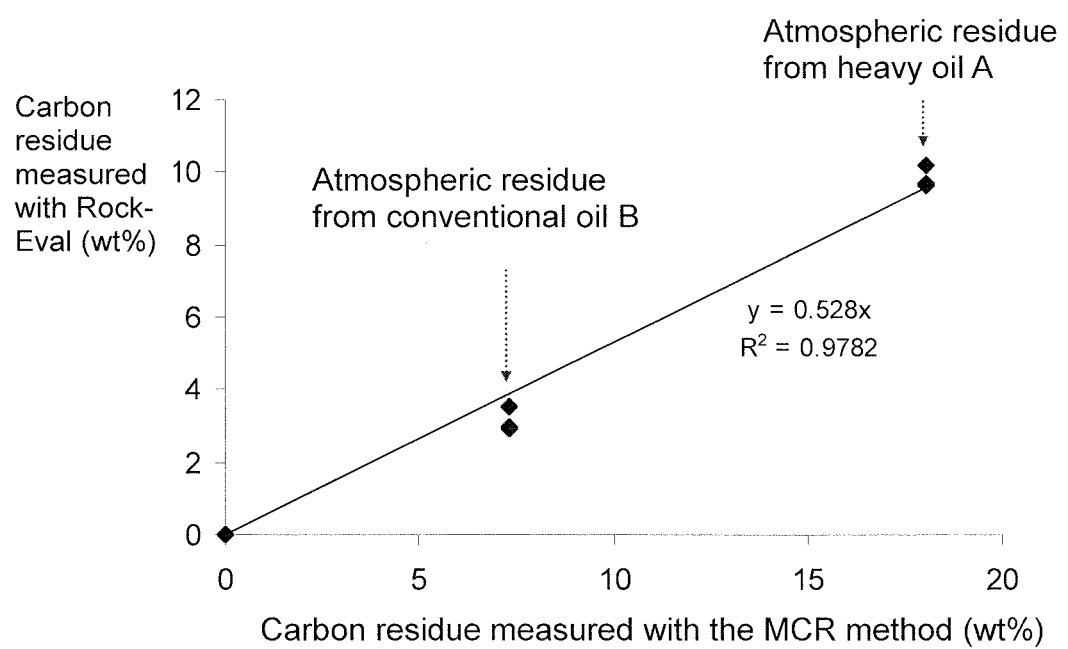

It has been noted that this non-pyrolyzable heavy fraction defined by the Rock-Eval analysis appears to be representative of the coke obtained after refining a petroleum feedstock. This is supported by the correlation observed between Rock-Eval parameter RC (residual carbon) and the carbon content of the residue obtained through ASTM D189 (CCR)

and ASTM D4530 (MCR), this residue being itself representative of the coke obtained by refining a petroleum product (FIG. 3).

From this conception of the origin of the Rock-Eval pyrolysis and oxidation effluents, four indicators describing the proportion of sulfur and carbon in the pyrolyzable heavy fraction (PHF) and in the coke can be defined.

Two indicators describe the proportion of sulfur in the pyrolyzable heavy fraction (PHF) and in the coke:

a. $S^{PHF} = Sulf_{S2b}/[Sulf_{S2b} + Sulf_{oxy}]$ expressed in g/g b. $S^{COKE} = Sulf_{oxy}/[Sulf_{S2b} + Sulf_{oxy}]$ expressed in g/g.

They satisfy the equality as follows:

$S^{PHF} + S^{COKE} = 1$.

Two indicators describe the proportion of carbon in the pyrolyzable heavy fraction (PHF) and in the coke:

c. $C^{PHF} = S2b*0.083/[S2b*0.083 + RC]$ expressed in g/g d. $C^{COKE} = RC/[S2b*0.083 + RC]$ expressed in g/g.

They satisfy the equality as follows:

$C^{PHF} + C^{COKE} = 1$.

A fifth indicator describes the richness in sulfur of the coke in relation to carbon, carbon being the main element in coke:

e. $Sulf_{oxy}/RC$ expressed in g/g.

These five indicators are used within the context of the present invention.

The interests and advantages of the five indicators of the method according to the invention, compared to existing methods of evaluation, are as follows:

a. There is no known method allowing, in a single analysis, to distinguish thermally extractable sulfur compounds from those thermally crackable and those thermally refractory.

b. To our knowledge, neither is there a method for simultaneously separating extractable carbon-containing species from those thermally crackable and those thermally refractory.

EXAMPLES

Eight petroleum product samples were analyzed with the Rock-Eval Sulfur device and their indicators $S^{PHF}$, $S^{COKE}$, $C^{PHF}$, $C^{COKE}$, $Sulf_{oxy}/RC$ were quantified.

These samples were:

a heavy oil A and a conventional oil B, their respective atmospheric residues, after atmospheric distillation, their respective vacuum residues, after vacuum distillation of the atmospheric residue, their respective asphaltenes fractions.

Figure 4:
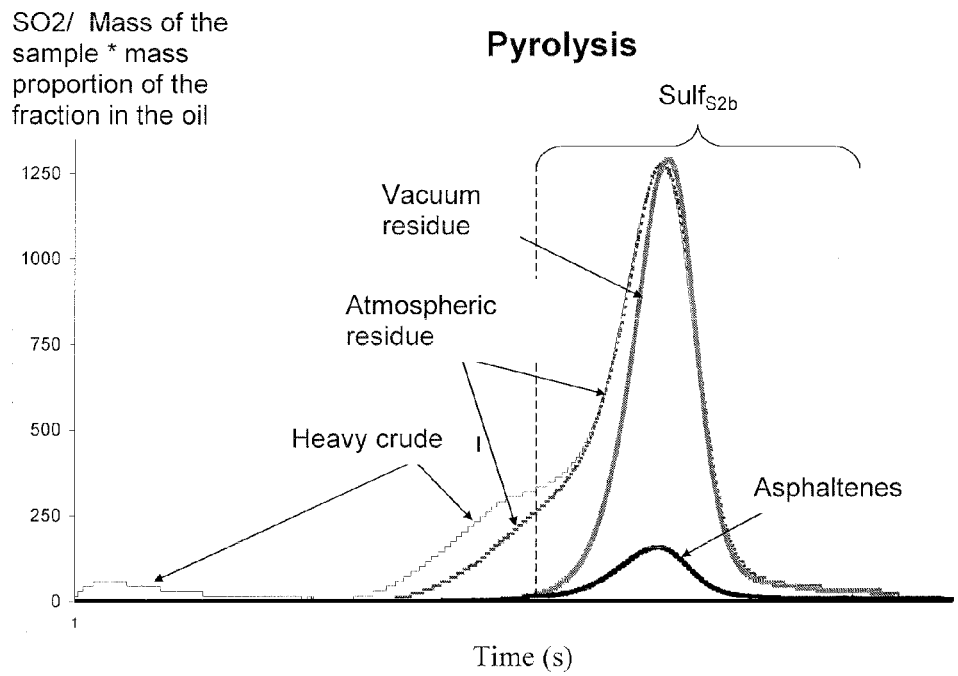
Figure 5:
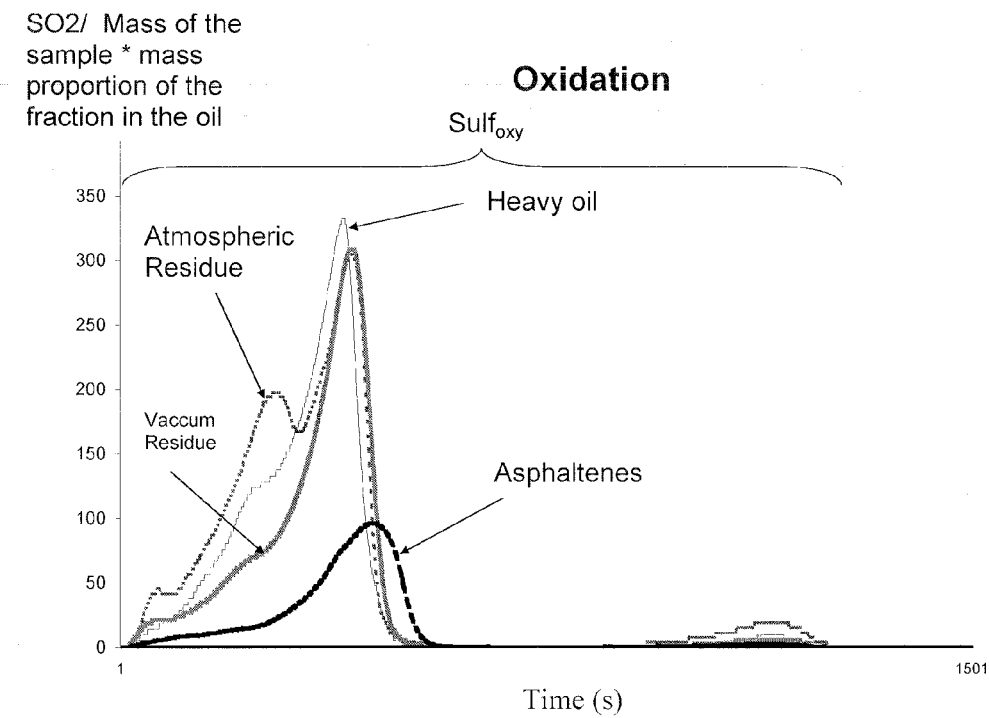

The results obtained are given in Tables 1 and 2 and in FIGS. 4 and 5.

TABLE 1

Characterization parameters of the carbon in the samples through Rock-Eval Sulfur analysis

| | TOC wt % | RC wt % | S2b mg/g | $C^{PHF}$ g/g | $Q^{COKE}$ g/g |
|---|---|---|---|---|---|
| Heavy oil A | 81.8 | 8.4 | 508 | 0.83 | 0.17 |
| Atmospheric residue A | 81.0 | 9.9 | 608 | 0.84 | 0.16 |

TABLE 1-continued

Characterization parameters of the carbon in the samples through Rock-Eval Sulfur analysis

| | TOC wt % | RC wt % | S2b mg/g | $C^{PHF}$ g/g | $Q^{COKE}$ g/g |
|---|---|---|---|---|---|
| Vacuum residue A | 76.8 | 16.0 | 724 | 0.79 | 0.21 |
| Asphaltenes A | 78.0 | 33.5 | 489 | 0.55 | 0.45 |
| Conventional oil B | 82.1 | 1.9 | 243 | 0.91 | 0.09 |
| Atmospheric residue B | 84.0 | 2.9 | 490 | 0.93 | 0.07 |
| Vacuum residue B | 80.3 | 6.1 | 849 | 0.92 | 0.08 |
| Asphaltenes B | 84.6 | 39.2 | 511.9 | 0.52 | 0.48 |

TABLE 2

Characterization parameters of the sulfur in the samples through Rock-Eval Sulfur analysis

| | Sulf wt % | $Sulf_{oxy}$ wt % | $Sulf_{S2b}$ wt % | $S^{PHF}$ g/g | $S^{COKE}$ g/g | $Sulf_{oxy}/RC$ g/g |
|---|---|---|---|---|---|---|
| Heavy oil A | 4.8 | 0.6 | 3.4 | 0.84 | 0.16 | 0.07 |
| Atmospheric residue A | 5.5 | 0.7 | 3.9 | 0.84 | 0.16 | 0.07 |
| Vacuum residue A | 6.2 | 1.0 | 5.1 | 0.83 | 0.17 | 0.06 |
| Asphaltenes A | 8.3 | 3.5 | 4.7 | 0.57 | 0.43 | 0.11 |
| Conventional oil B | 1.8 | 0.0 | 1.1 | 0.97 | 0.03 | 0.02 |
| Atmospheric residue B | 2.9 | 0.1 | 1.8 | 0.96 | 0.04 | 0.03 |
| Vacuum residue B | 3.4 | 0.2 | 3.1 | 0.95 | 0.05 | 0.03 |
| Asphaltenes B | 4.1 | 1.5 | 2.6 | 0.63 | 0.37 | 0.04 |

FIG. 4 shows that only part of the pyrolyzable heavy sulfur compounds of the oil are present in the distillation residues and in the asphaltenes. However, for the atmospheric residue, it can be seen in FIG. 4 that it contains nearly as many heavy pyrolyzable sulfur compounds as the initial oil.

FIG. 5 suggests that some sulfur compounds making up the pyrolysis residues of the distillation residues and the asphaltenes are different from those of the oil pyrolysis residue.

If we compare the five indicators $S^{PHF}$, $S^{COKE}$, $C^{PHF}$, $C^{COKE}$, $Sulf_{oxy}/RC$ in Tables 1 and 2, for the crude oils, their atmospheric distillation residues and their vacuum distillation residues, we observe very close results. By comparison, these five indicators applied to the asphaltenes show very different results from those obtained for the crude oils and the distillation residues.

This clearly shows that the values of the indicators according to the invention ($S^{PHF}$, $S^{COKE}$, $C^{PHF}$, $C^{COKE}$, $Sulf_{oxy}/RC$), obtained on the crude oil by means of a Rock-Eval analysis ($S^{2b}$, $Sulf_{S2b}$, $Sulf_{oxy}$, RC), allow to estimate those of the distillation residues. These fast and therefore inexpensive estimations are very advantageous for evaluating the thermal reactivity of the sulfur and the carbon of the residues of a feedstock to be refined.

The invention claimed is:

1. A method of estimating, for crude oil, values representative of the distribution of sulfur and carbon in atmospheric and vacuum distillation residues, and a value representative of the sulfur in the coke, a method wherein the following stages are carried out:

from a crude oil sample, measuring at least parameters S2b, $Sulf_{S2b}$, RC, $Sulf_{oxy}$ using a device comprising at least one oven for pyrolysis in an inert atmosphere and at least one oxidation oven, said device comprising a sulfur measurement module, S2b being the mass proportion of heavy pyrolyzable compounds contained in said sample, $Sulf_{S2b}$ being the mass proportion of sulfur in the heavy pyrolyzable compounds contained in said sample, RC being the mass proportion of carbon of the pyrolysis residue of said sample, and $Sulf_{oxy}$ being the mass proportion of sulfur in the pyrolysis residue of said sample, deducing from said measurements of said parameters said values of the sulfur and carbon distributions in the distillation residues, and a sulfur content in relation to the carbon content in the coke.

2. A method as claimed in claim 1, wherein said representative values are determined as follows:

$S^{PHF}=Sulf_{S2b}/[Sulf_{S2b}+Sulf_{oxy}]$, where $S^{PHF}$ corresponds to the proportion of sulfur in the pyrolyzable heavy fraction, with said parameters $Sulf_{S2b}$, $Sulf_{S2b}$ and $Sulf_{oxy}$ expressed in gram of sulfur per 100 grams of said sample, $S^{COKE}=Sulf_{oxy}/[Sulf_{S2b}+Sulf_{oxy}]$, where $S^{COKE}$ corresponds to the proportion of sulfur in the coke, with said parameters $Sulf_{S2b}$, $Sulf_{S2b}$ and $Sulf_{oxy}$ expressed in gram of sulfur per 100 grams of said sample, with $S^{PHF}+S^{COKE}=1$, $C^{PHF}=S2b*0.083/[S2b*0.083+RC]$, where $C_{PHF}$ corresponds to the proportion of carbon in the pyrolyzable heavy fraction, with said parameters S2b expressed in gram of organic compounds per 1000 grams of said sample and RC expressed in gram of carbon per 100 grams of said sample, $C^{COKE}=RC/[S2b*0.083+RC]$, where $C^{COKE}$ corresponds to the proportion of carbon in the coke, with said parameters S2b expressed in gram of organic compounds per 1000 grams of said sample and RC expressed in gram of carbon per 100 grams of said sample, with $C^{PHF}+C^{COKE}=1$.

3. A method as claimed in claim 1, wherein the value representative of the richness in sulfur in relation to the carbon content in the coke is determined as follows:

$Sulf_{oxy}/RC$, with said parameters $Sulf_{oxy}$ and RC expressed in gram of sulfur and carbon respectively per 100 grams of said sample.

4. A method of estimating, for crude oil, values representative of the distribution of sulfur and carbon in atmospheric and vacuum distillation residues, and a value representative of the sulfur in the coke, a method wherein the following stages are carried out:

from a crude oil sample, measuring at least parameters S2b, $Sulf_{S2b}$, RC, $Sulf_{oxy}$ using a device comprising at least one oven for pyrolysis in an inert atmosphere and at least one oxidation oven, said device comprising a sulfur measurement module, S2b being the mass proportion of heavy pyrolyzable compounds contained in said sample, $Sulf_{S2b}$ being the mass proportion of sulfur in the heavy pyrolyzable compounds contained in said sample, RC being the mass proportion of carbon of the pyrolysis residue of said sample, and $Sulf_{oxy}$ being the mass proportion of sulfur in the pyrolysis residue of said sample, deducing from said measurements of said parameters said values of the sulfur and carbon distributions in the distillation residues, and a sulfur content in relation to the carbon content in the coke, wherein said representative values of the sulfur and carbon distributions in the distillation residues are determined as follows:

$S^{PHF}=Sulf_{S2b}/[Sulf_{S2b}+Sulf_{oxy}]$, where $S^{PHF}$ corresponds to the proportion of sulfur in the pyrolyzable heavy fraction, with said parameters $Sulf_{S2b}$, $Sulf_{S2b}$ and $Sulf_{oxy}$ expressed in gram of sulfur per 100 grams of said sample, $S^{COKE}=Sulf_{oxy}$ $[Sulf_{S2b}+Sulf_{oxy}]$, where $S^{COKE}$ corresponds to the proportion of sulfur in the coke, with said parameters $Sulf_{S2b}$, $Sulf_{S2b}$ and $Sulf_{oxy}$ expressed in gram of sulfur per 100 grams of said sample, with $S^{PHF}+S^{COKE}=1$, $C^{PHF}=S2b*0.083/[S2b*0.083+RC]$, where $C^{PHF}$ corresponds to the proportion of carbon in the pyrolyzable heavy fraction, with said parameters S2b expressed in gram of organic compounds per 1000 grams of said sample and RC expressed in gram of carbon per 100 grams of said sample, $C^{COKE}=RC/[S2b*0.083+RC]$, where $C^{COKE}$ corresponds to the proportion of carbon in the coke, with said parameters S2b expressed in gram of organic compounds per 1000 grams of said sample and RC expressed in gram of carbon per 100 grams of said sample, with $C^{PHF}+C^{COKE}=1$, and wherein the value representative of the richness in sulfur in relation to the carbon content in the coke is determined as follows:

$Sulf_{oxy}/RC$, with said parameters $Sulf_{oxy}$ and RC expressed in gram of sulfur and carbon respectively per 100 grams of said sample.

* * * * *